(12) United States Patent
Takahashi et al.

(10) Patent No.: US 10,188,561 B2
(45) Date of Patent: Jan. 29, 2019

(54) NONWOVEN FABRIC LAMINATE, ABSORBENT ARTICLE HAVING NONWOVEN FABRIC LAMINATE, AND PROCESS FOR PRODUCING NONWOVEN FABRIC LAMINATE

(71) Applicant: LIVEDO CORPORATION, Ehime (JP)

(72) Inventors: Yuki Takahashi, Tokushima (JP); Kenji Nakaoka, Osaka (JP)

(73) Assignee: LIVEDO CORPORATION, Ehime (JP)

( * ) Notice: Subject to any disclaimer, the term of this patent is extended or adjusted under 35 U.S.C. 154(b) by 372 days.

(21) Appl. No.: 14/917,069

(22) PCT Filed: Sep. 26, 2014

(86) PCT No.: PCT/JP2014/075562
§ 371 (c)(1),
(2) Date: Mar. 7, 2016

(87) PCT Pub. No.: WO2015/046400
PCT Pub. Date: Apr. 2, 2015

(65) Prior Publication Data
US 2016/0213531 A1 Jul. 28, 2016

(30) Foreign Application Priority Data
Sep. 30, 2013 (JP) .................. 2013-203773

(51) Int. Cl.
*A61F 13/514* (2006.01)
*B32B 5/26* (2006.01)
(Continued)

(52) U.S. Cl.
CPC .. *A61F 13/51476* (2013.01); *A61F 13/15699* (2013.01); *A61F 13/15731* (2013.01);
(Continued)

(58) Field of Classification Search
CPC .......... A61F 13/51476; A61F 13/51478; A61F 13/15699; A61F 13/15731; A61F 13/49009; B32B 5/02; B32B 5/26; B32B 555/00; B32B 555/02; B32B 37/10; B32B 38/06
See application file for complete search history.

(56) References Cited

U.S. PATENT DOCUMENTS

| 4,720,415 A | 1/1988 | Vander Wielen et al. |
| 5,455,110 A | 10/1995 | Connor |

(Continued)

FOREIGN PATENT DOCUMENTS

| CN | 1655748 | 8/2005 |
| JP | 52-42916 | 10/1977 |

(Continued)

OTHER PUBLICATIONS

Office Action dated Sep. 13, 2017 in European Application No. 14847969.4.
(Continued)

*Primary Examiner* — Jacqueline Stephens
(74) *Attorney, Agent, or Firm* — Wenderoth, Lind & Ponack, L.L.P.

(57) ABSTRACT

An absorbent article comprising an exterior sheet formed of a nonwoven fabric laminate (1) in which a first nonwoven fabric layer (2), a second nonwoven fabric layer (3) and a third nonwoven fabric layer (4) are laminated from the outer side, wherein the first nonwoven fabric layer (2), the second nonwoven fabric layer (3) and the third nonwoven fabric layer (4) are joined to each other at a first joining part (6) by heat-embossing, and the second nonwoven fabric layer (3) and the third nonwoven fabric layer (4) are further joined to each other at a second joining part (7) by heat-embossing.

13 Claims, 6 Drawing Sheets

(51) Int. Cl.

| | |
|---|---|
| *D04H 1/559* | (2012.01) |
| *B32B 5/02* | (2006.01) |
| *A61F 13/15* | (2006.01) |
| *A61F 13/49* | (2006.01) |
| *B32B 37/06* | (2006.01) |
| *B32B 37/10* | (2006.01) |
| *B32B 38/06* | (2006.01) |

(52) U.S. Cl.
CPC .. *A61F 13/49009* (2013.01); *A61F 13/51478* (2013.01); *B32B 5/022* (2013.01); *B32B 5/26* (2013.01); *B32B 37/06* (2013.01); *B32B 37/10* (2013.01); *B32B 38/06* (2013.01); *D04H 1/559* (2013.01); *B32B 2250/03* (2013.01); *B32B 2250/20* (2013.01); *B32B 2307/54* (2013.01); *B32B 2307/724* (2013.01); *B32B 2307/726* (2013.01); *B32B 2555/00* (2013.01); *B32B 2555/02* (2013.01)

(56) References Cited

U.S. PATENT DOCUMENTS

| | | |
|---|---|---|
| 5,688,157 A | 11/1997 | Bradley et al. |
| 5,882,769 A | 3/1999 | McCormack et al. |
| 2002/0026660 A1 | 3/2002 | Goda |
| 2005/0065490 A1 | 3/2005 | Shimoe et al. |
| 2013/0237938 A1* | 9/2013 | Autran ............. A61F 13/51464 604/365 |

FOREIGN PATENT DOCUMENTS

| | | |
|---|---|---|
| JP | 62-33889 | 2/1987 |
| JP | 6-255006 | 9/1994 |
| JP | 2002-67199 | 3/2002 |
| JP | 2007-29612 | 2/2007 |
| JP | 2008-152051 | 7/2008 |
| JP | 2009-207698 | 9/2009 |
| JP | 2009-297096 | 12/2009 |

OTHER PUBLICATIONS

Extended European Search Report dated Mar. 13, 2017 in corresponding European Application No. 14847969.4.
International Search Report dated Dec. 16, 2014 in International (PCT) Application No. PCT/JP2014/075562.
Office Action dated Jun. 5, 2018 in Chinese Patent Application No. 201480051673.8, with English-language translation.
Notice of Reasons for Rejection dated Sep. 5, 2018 in corresponding Japanese Application No. 2015-539370, with English translation.

* cited by examiner

[Fig. 1]
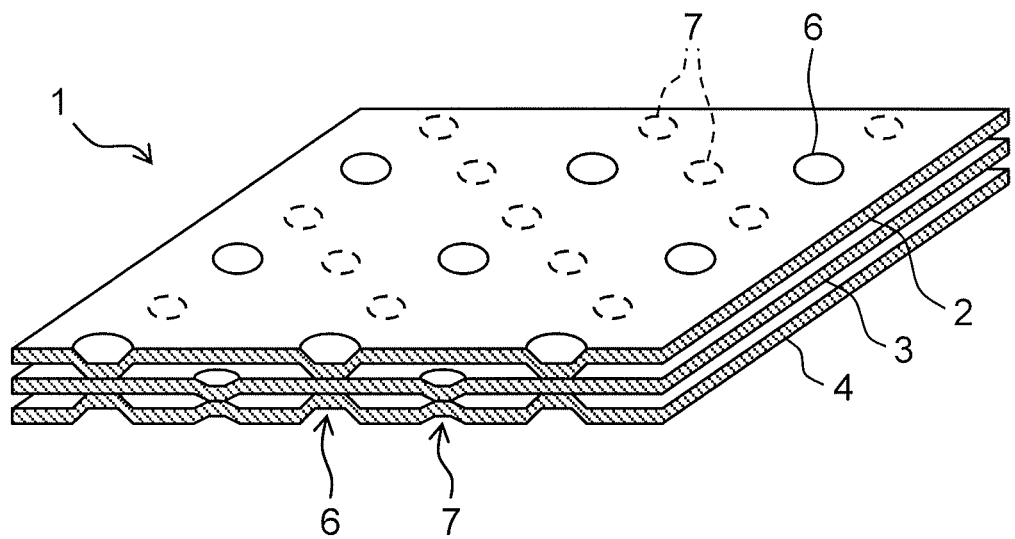
[Fig. 2]
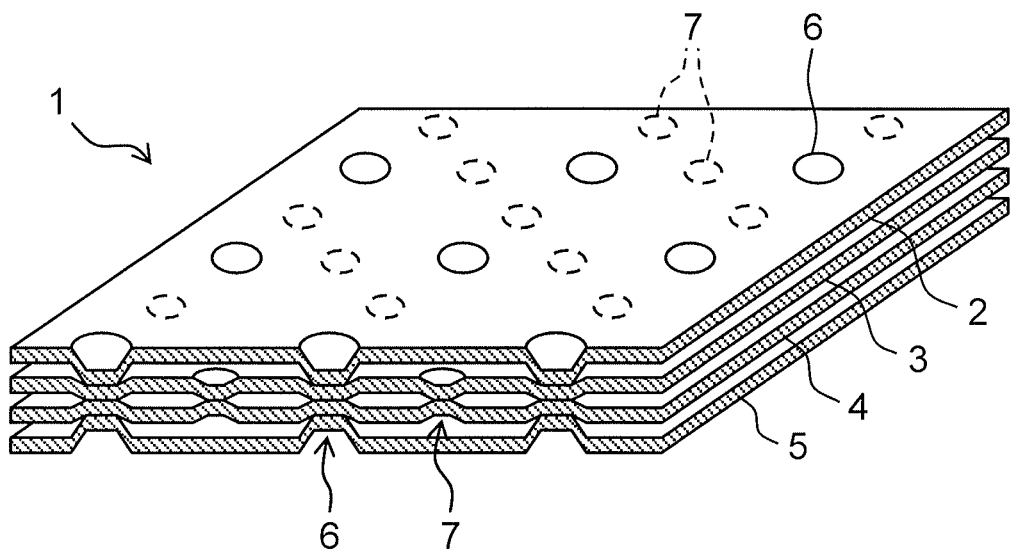

[Fig. 3]
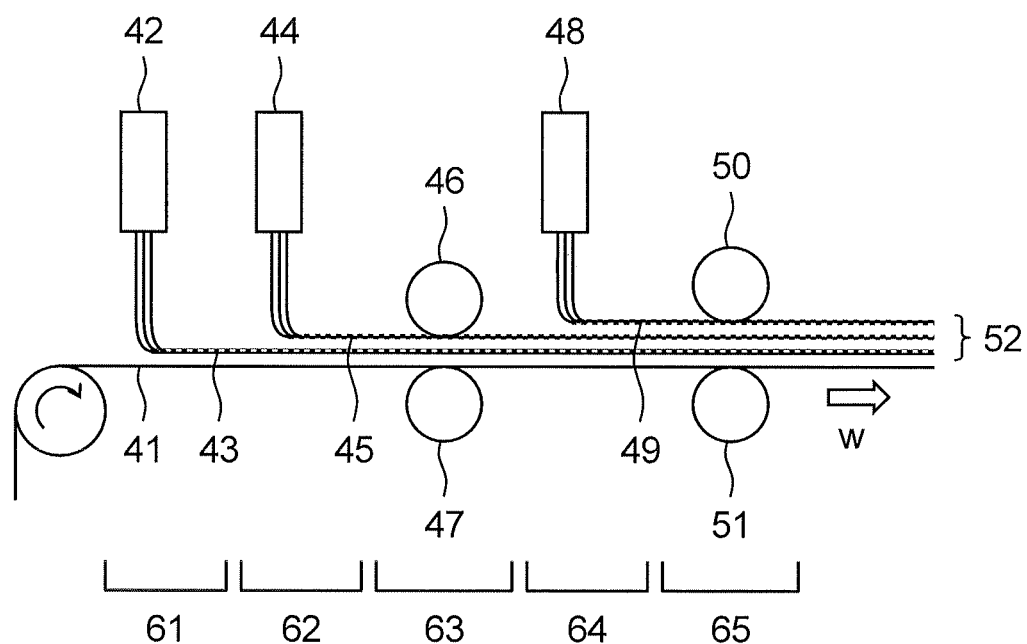

[Fig. 4]
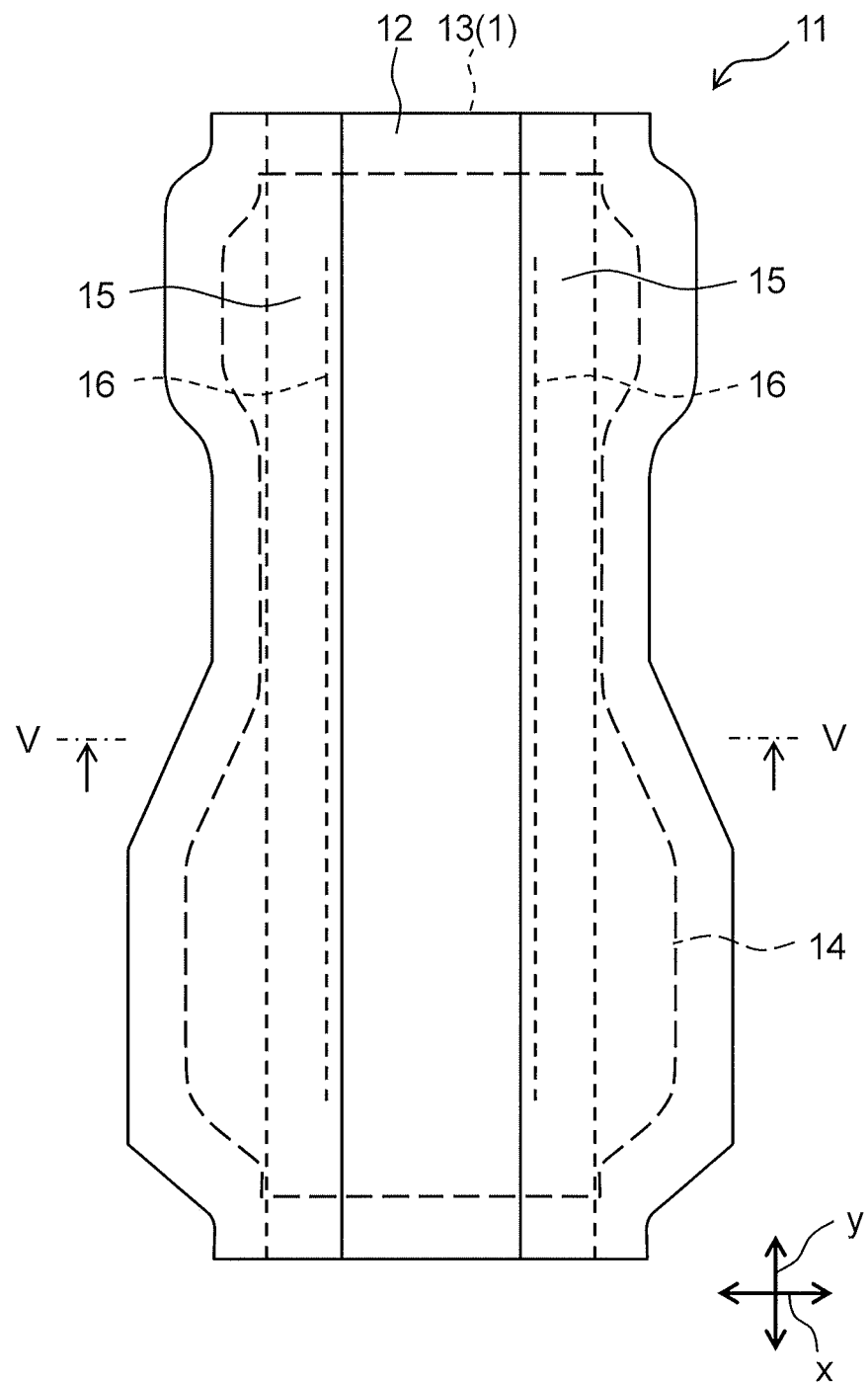

[Fig. 5]
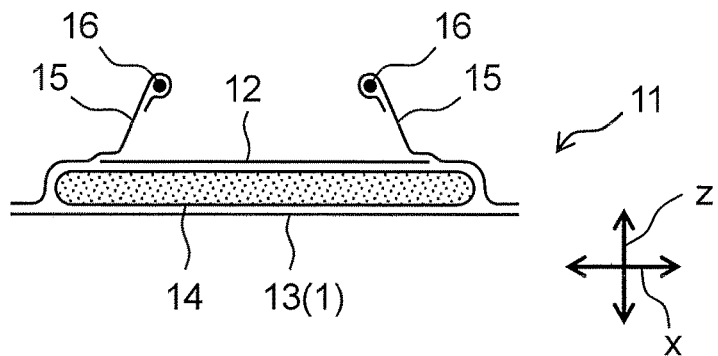
[Fig. 6]
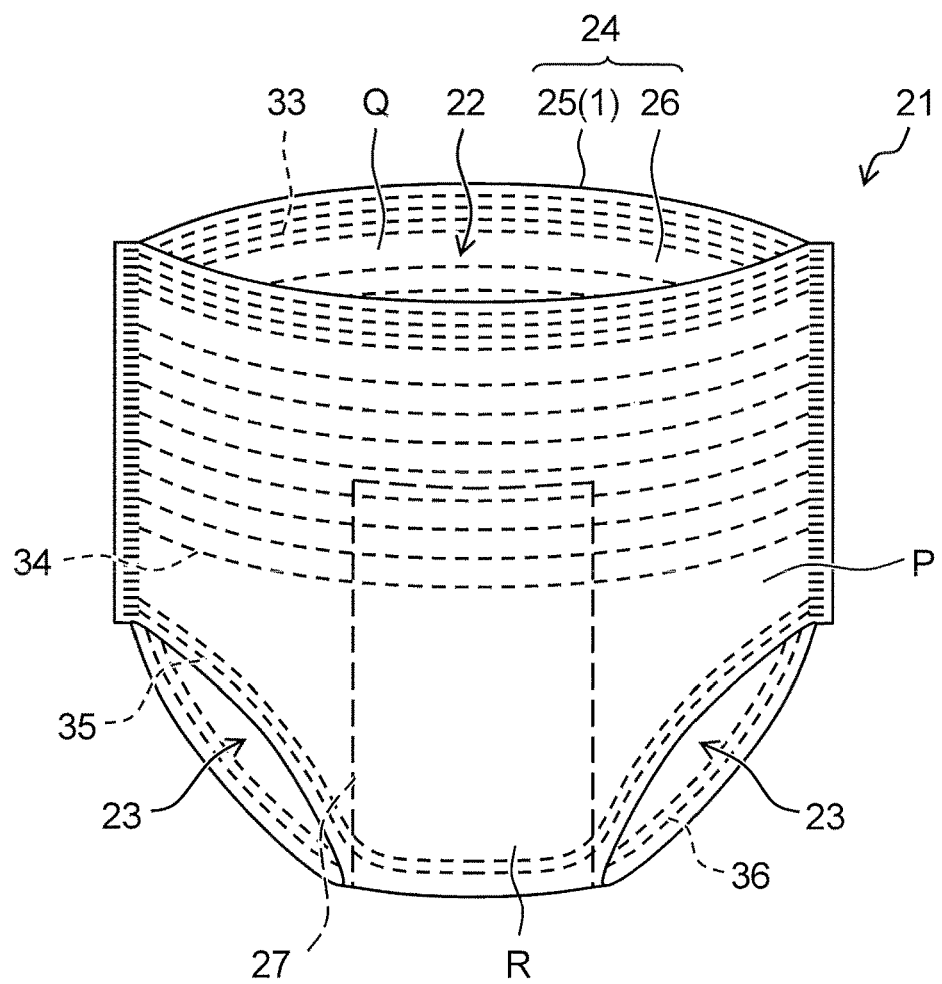

[Fig. 7]
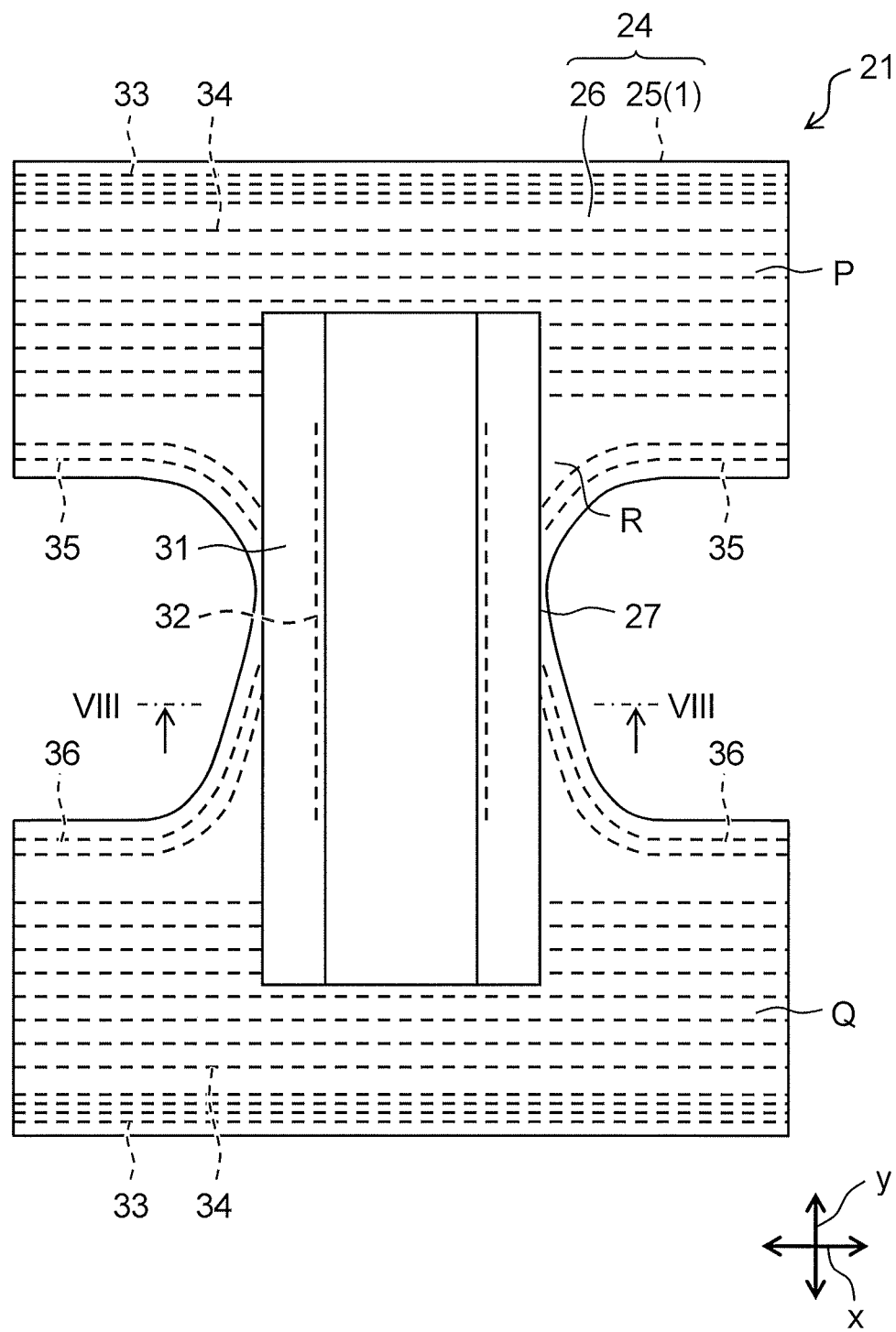

[Fig. 8]
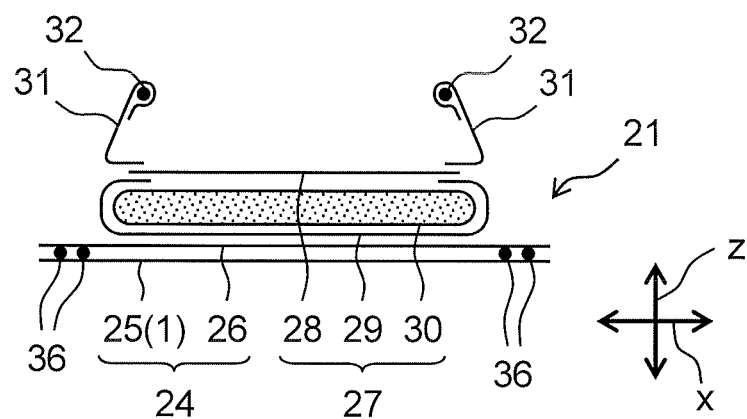

NONWOVEN FABRIC LAMINATE, ABSORBENT ARTICLE HAVING NONWOVEN FABRIC LAMINATE, AND PROCESS FOR PRODUCING NONWOVEN FABRIC LAMINATE

TECHNICAL FIELD

The present invention relates to a nonwoven fabric laminate, a production method therefore and an absorbent article having the nonwoven fabric laminate such as a disposable diaper, an incontinence pad (including a light incontinence pad) and a sanitary napkin.

BACKGROUND ART

A nonwoven fabric is widely used in life materials and industrial materials, and various kinds of nonwoven fabrics are known. In absorbent articles such as disposable diapers, nonwoven fabrics are widely used as a constituent member thereof, and optimal nonwoven fabrics according to the usage are variously examined. For example, a sheet member disposed on an outer side of an absorbent article (an exterior sheet) is a member which a user often touches by hand and strongly contacts to a wearer's underwear or clothing, and hence, it is preferred that it has sufficient strength and good hand feeling. Even in other applications, nonwoven fabrics have many opportunities to be touched by hand, and it is preferably provided with such characteristics. As a method for increasing the strength of nonwoven fabrics, for example, Patent Literature 1 discloses a disposable diaper provided with a sheet member made of a nonwoven fabric of which an outer surface is embossed, and describes that the emboss of the nonwoven fabric increases interfiber strength and suppresses fuzzing.

CITATION LIST

Patent Literature

Patent Literature 1

Japanese Unexamined Laid-open Patent Application Publication No. 2007-29612

SUMMARY OF INVENTION

Technical Problem

The present invention has been achieved in view of the above circumstances, and the object of the present invention is to provide a nonwoven fabric laminate that is excellent in conflicting both properties of strength and hand feeling, a production process therefor, and further, an absorbent article comprising an exterior sheet provided on an outer side thereof, that is excellent in both properties of strength and hand feeling.

Solution to Problem

A nonwoven fabric laminate of the present invention which solves the above problems is the nonwoven fabric laminate in which a first nonwoven fabric layer, a second nonwoven fabric layer and a third nonwoven fabric layer are laminated in this order, wherein the first nonwoven fabric layer, the second nonwoven fabric layer and the third nonwoven fabric layer are joined to each other at a first joining part by heat-embossing, and the second nonwoven fabric layer and the third nonwoven fabric layer are further joined to each other at a second joining part by heat-embossing. In the nonwoven fabric laminate of the present invention, since the second nonwoven fabric layer and the third nonwoven fabric layer are joined to each other at both the first joining part and the second joining part by heat-embossing, strength of the nonwoven fabric laminate can be increased. And, since the first nonwoven fabric layer is joined to the second nonwoven fabric layer only at the first joining part, joining parts formed by heat-embossing are decreased and hand feeling of the first nonwoven fabric layer side of the nonwoven fabric laminate can be made good.

It is preferred that an area of the one first joining part is larger than that of the one second joining part. When the first joining part is provided in this manner, the first nonwoven fabric layer, the second nonwoven fabric layer and the third nonwoven fabric layer are firmly joined to each other at the first joining part, thereby increasing integrity of the nonwoven fabric laminate.

It is preferred that each of the first nonwoven fabric layer, the second nonwoven fabric layer and the third nonwoven fabric layer is made of a spunbonded nonwoven fabric or an air-through nonwoven fabric. When each of the first nonwoven fabric layer, the second nonwoven fabric layer and the third nonwoven fabric layer is made of a spunbonded nonwoven fabric or an air-through nonwoven fabric, breathability of the nonwoven fabric laminate is increased and internal humidity is easily decreased in the case where the nonwoven fabric laminate is applied to various applications. In this case, the first joining part preferably has a shape that is shorter in an orientation direction of fibers constituting the nonwoven fabric than in an orthogonal direction thereof. When the first joining part is provided in this manner, breaking strength of the spunbonded nonwoven fabric or the air-through nonwoven fabric with respect to a direction orthogonal to the fiber orientation direction can be increased and integrity of the first nonwoven fabric layer, the second nonwoven fabric layer and the third nonwoven fabric layer is easily maintained.

The first joining part and the second joining part may have a different shape from each other. When the first joining part and the second joining part are formed in this manner, it becomes possible to give a desired physical property to the nonwoven fabric laminate in accordance with an actual usage. For example, it is possible to determine the shape of the first joining part from the viewpoint of ensuring the integrity of the nonwoven fabric laminate and determine the shape of the second joining part from the viewpoint of increasing the strength of the nonwoven fabric laminate.

The present invention also provides a process for producing a nonwoven fabric laminate. A process for producing a nonwoven fabric laminate of the present invention comprises the steps in the sequence set forth: forming a third nonwoven fabric layer; forming a second nonwoven fabric layer on the third nonwoven fabric layer; heat-embossing the second nonwoven fabric layer and the third nonwoven fabric layer to join to each other at a second joining part; forming a first nonwoven fabric layer on the second nonwoven fabric layer; and heat-embossing the first nonwoven fabric layer, the second nonwoven fabric layer and the third nonwoven fabric layer to join to each other at a first joining part. According to the process for producing a nonwoven fabric laminate of the present invention, the nonwoven fabric laminate of the present invention can be easily manufactured.

The nonwoven fabric laminate of the present invention is preferably applied to an exterior sheet located on an outer side of an absorbent article, whereby hand feeling of the exterior sheet can be improved while strength thereof is increased. That is, an absorbent article of the present invention comprises an exterior sheet formed of a plurality of nonwoven fabric layers, wherein the exterior sheet is located on an outer side of the absorbent article and has a first nonwoven fabric layer, a second nonwoven fabric layer and a third nonwoven fabric layer from the outer side of the absorbent article, the first nonwoven fabric layer, the second nonwoven fabric layer and the third nonwoven fabric layer are joined to each other at a first joining part by heat-embossing, and the second nonwoven fabric layer and the third nonwoven fabric layer are further joined to each other at a second joining part by heat-embossing. In the absorbent article of the present invention, since the second nonwoven fabric layer and the third nonwoven fabric layer of the exterior sheet are joined to each other at both the first joining part and the second joining part by heat-embossing, strength of the exterior sheet can be increased. And, since the first nonwoven fabric layer is provided on the outer side of the second nonwoven fabric layer and is joined to the second nonwoven fabric layer at the first joining part, joining parts formed by heat-embossing are decreased and hand feeling of the exterior sheet can be made good.

In the case that an elastic member is disposed to a skin-facing side of the exterior sheet, it is preferred that the first joining part has a shape that is shorter in an extending direction of the elastic member than in an orthogonal direction thereof. When the first joining part is provided in this manner, many wrinkles extending in a direction orthogonal to the extending direction of the elastic member are easily formed in the exterior sheet, and the elastic member can be made hardly to be seen from the outside of the exterior sheet. From the same viewpoint, it is also preferable that a plurality of the first joining parts are aligned in an extending direction of the elastic member and an orthogonal direction thereof, and a distance between the first joining parts in the extending direction is wider than that in the orthogonal direction.

In the case that the absorbent article is a pants-type disposable diaper and an elastic member extending in a width direction of the diaper is disposed at a body circumference part of the diaper between the exterior sheet and an inner sheet provided on a skin-facing side of the exterior sheet, it is preferred that the first joining part has a shape that is longer in a longitudinal direction of the diaper than in the width direction of the diaper. When the first joining part is provided in this manner, many wrinkles extending in the longitudinal direction are formed in the exterior sheet, and the elastic member can be made hardly to be seen from the outside of the exterior sheet. In this case, from the same viewpoint, it is also preferable that a plurality of the first joining parts are aligned in the longitudinal direction of the diaper and the width direction of the diaper, and a distance between the first joining parts in the width direction of the diaper is wider than that in the longitudinal direction of the diaper.

Advantageous Effects of Invention

In the nonwoven fabric laminate of the present invention, the first nonwoven fabric layer, the second nonwoven fabric layer and the third nonwoven fabric layer are joined to each other at the first joining part by heat-embossing, and the second nonwoven fabric layer and the third nonwoven fabric layer are further joined to each other at the second joining part by heat-embossing. Therefore, strength of the nonwoven fabric laminate is ensured by the heat-emboss of the second nonwoven fabric layer and the third nonwoven fabric layer at the first and second joining part, and hand feeling of the first nonwoven fabric layer side of the nonwoven fabric laminate can be made good by heat-embossing the first nonwoven fabric layer only at the first joining part. Further, according to the absorbent article of the present invention in which the nonwoven fabric laminate of the present invention is used for the exterior sheet, strength of the exterior sheet is ensured and hand feeling thereof is made good.

BRIEF DESCRIPTION OF THE DRAWINGS

FIG. 1 represents an example of a nonwoven fabric laminate and shows a perspective view of the nonwoven fabric laminate.

FIG. 2 represents another example of a nonwoven fabric laminate and shows a perspective view of the nonwoven fabric laminate.

FIG. 3 shows a schematic view of a process for producing the nonwoven fabric laminate shown in FIG. 1.

FIG. 4 shows a plan view of a skin-facing side of an incontinence pad as an absorbent article.

FIG. 5 shows a cross-sectional view along a line V-V of the incontinence pad shown in FIG. 4.

FIG. 6 shows a perspective view of a pants-type disposable diaper as an absorbent article.

FIG. 7 shows a plan view of the pants-type disposable diaper shown in FIG. 6 in a developed state where a front part and a rear part are disjoined.

FIG. 8 shows a cross-sectional view along a line VIII-VIII of the pants-type disposable diaper shown in FIG. 7.

DESCRIPTION OF THE PREFERRED EMBODIMENTS

[Nonwoven Fabric Laminate]

A nonwoven fabric laminate of the present invention comprises a plurality of nonwoven fabric layers, wherein the nonwoven fabric layers which are laminated adjacently are joined to each other by heat-embossing. The nonwoven fabric laminate of the present invention can be made to have good hand feeling while ensuring strength, by appropriately setting a pattern of the heat-emboss for boding the nonwoven fabric layers to each other.

The nonwoven fabric laminate comprises a first nonwoven fabric layer, a second nonwoven fabric layer and a third nonwoven fabric layer. The first nonwoven fabric layer, the second nonwoven fabric layer and the third nonwoven fabric layer are laminated in this order, and the first nonwoven fabric layer preferably becomes a surface which a user mainly touches by hand. That is, it is preferred that the first nonwoven fabric layer faces outward.

The nonwoven fabric laminate of the present invention can be applied to conventionally-known applications of nonwoven fabrics, that include, for example, absorbent articles such as a disposable diaper and an incontinence pad; covers such as a pillow cover, a shoe cover and a suit cover; bags such as a storage bag; protective clothing such as a protective suit and a surgical gown; and sheets such as a drape, an agricultural sheet, a wet tissue and a wet towel. In the case of applying to absorbent articles, covers, bags and protective clothing, it is preferred that the first nonwoven fabric layer is located on an outer surface thereof, whereby hand feeling of the nonwoven fabric product can be made good. In the case of applying to sheets, the first nonwoven fabric layer is preferably located on an outer surface thereof during use, or the nonwoven fabric laminate may be folded so that the first nonwoven fabric layer is located outside.

In the nonwoven fabric laminate, the first nonwoven fabric layer, the second nonwoven fabric layer and the third nonwoven fabric layer are joined to each other at a first joining part by heat-embossing, and the second nonwoven fabric layer and the third nonwoven fabric layer are further joined to each other at a second joining part by heat-embossing. That is, the first nonwoven fabric layer, the second nonwoven fabric layer and the third nonwoven fabric layer are heat-embossed together at the first joining part to be joined to each other. The second joining part is formed by heat-embossing the second nonwoven fabric layer and the third nonwoven fabric layer, and the first nonwoven fabric layer and the second nonwoven fabric layer are not joined by embossing at the second joining part.

Since the nonwoven fabric laminate is configured in the above manner, both strength and hand feeling can be enhanced. Strength of a nonwoven fabric is generally increased by heat-embossing, and for example, the nonwoven fabric can be made to be hardly broken even when it is pulled; however, the nonwoven fabric tends to be hardened at the heat-embossed part, that deteriorates hand feeling of the nonwoven fabric. Nevertheless, in the present invention, among the nonwoven fabric layers constituting the nonwoven fabric laminate, the second nonwoven fabric layer and the third nonwoven fabric layer are joined at both the first joining part and the second joining part by heat-embossing, whereby strength of the nonwoven fabric laminate can be increased. And, the first nonwoven fabric layer is joined to the second nonwoven fabric layer only at the first joining part, whereby joining parts formed by heat-embossing are decreased and hand feeling of the first nonwoven fabric layer side of the nonwoven fabric laminate can be made good. In addition, since the first nonwoven fabric layer, the second nonwoven fabric layer and the third nonwoven fabric layer are heat-embossed together at the first joining part, integrity of the nonwoven fabric layers constituting the nonwoven fabric laminate can be ensured. Further, since the nonwoven fabric laminate of the present invention is formed such that the joining pattern of the first nonwoven fabric layer with the second nonwoven fabric layer is different from that of the second nonwoven fabric layer with the third nonwoven fabric layer, interlayer distances between the respective nonwoven fabric layers are variously changed, that makes degree of transmission or diffusion of light through the nonwoven fabric laminate uneven properly, whereby a visual shielding property through the nonwoven fabric laminate can be increased.

In the present invention, the nonwoven fabric laminate are formed by laminating the first nonwoven fabric layer, the second nonwoven fabric layer and the third nonwoven fabric layer and is handled as a single sheet member. Therefore, in the nonwoven fabric laminate, it is preferred that the second nonwoven fabric layer is provided between the first nonwoven fabric layer and the third nonwoven fabric layer, the second nonwoven fabric layer is provided adjacent to the first nonwoven fabric layer and the third nonwoven fabric layer, and any other member is not provided both between the first nonwoven fabric layer and the second nonwoven fabric layer and between the second nonwoven fabric layer and the third nonwoven fabric layer. In the case that a fourth nonwoven fabric layer is provided as described below, it is preferred that the fourth nonwoven fabric layer is provided adjacent to the third nonwoven fabric layer and any other member is not also provided between the third nonwoven fabric layer and the fourth nonwoven fabric layer.

In the nonwoven fabric laminate, a plurality of the nonwoven fabric layers are laminated and integrated by heat-embossing. In the nonwoven fabric laminate, at the first joining part and the second joining part that are heat-embossed, certain embossed patterns are formed by pressing while the adjacent nonwoven fabric layers are joined to each other by thermal fusion bonding. Heat-embossing may be conducted by bringing a heated heat-transfer material contact with the nonwoven fabric layer to melt a part of the nonwoven fabric layer or by bringing a ultrasonic transducer contact with the nonwoven fabric layer to melt a part of the nonwoven fabric layer with ultrasonic vibration, in the state where the nonwoven fabric layers are laminated.

The nonwoven fabric laminate may further comprise another layer in addition to the first nonwoven fabric layer, the second nonwoven fabric layer and the third nonwoven fabric layer. The another layer is preferably a nonwoven fabric layer. In the case that the another layer is provided on an outer side of the first nonwoven fabric layer, it is preferred that the another layer is joined to the first nonwoven fabric layer only at the first joining part by heat-embossing.

The nonwoven fabric laminate may further comprise a fourth nonwoven fabric layer in addition to the first nonwoven fabric layer, the second nonwoven fabric layer and the third nonwoven fabric layer. In this case, the first nonwoven fabric layer, the second nonwoven fabric layer, the third nonwoven fabric layer and the fourth nonwoven fabric layer are laminated in this order. In the case that the nonwoven fabric laminate comprises the fourth nonwoven fabric layer, it is preferred that the first nonwoven fabric layer, the second nonwoven fabric layer, the third nonwoven fabric layer and the fourth nonwoven fabric layer are joined to each other at the first joining part by heat-embossing, and the second nonwoven fabric layer and the third nonwoven fabric layer are further joined to each other at second joining part by heat-embossing. When the nonwoven fabric laminate is configured in this manner, hand feeling of both the first nonwoven fabric layer side and the fourth nonwoven fabric layer side of the nonwoven fabric laminate can be made good. That is, the first nonwoven fabric layer is joined to the second nonwoven fabric layer only at the first joining part and the fourth nonwoven fabric layer is joined to the third nonwoven fabric layer only at the first joining part, whereby joining parts formed by heat-embossing are decreased and hand feeling of both the first nonwoven fabric layer side and the fourth nonwoven fabric layer side of the nonwoven fabric laminate can be made good. Meanwhile, the second nonwoven fabric layer and the third nonwoven fabric layer are joined at both the first joining part and the second joining part by heat-embossing, whereby strength of the nonwoven fabric laminate can be increased. In addition, integrity of the nonwoven fabric layers constituting the nonwoven fabric laminate is ensured by heat-embossing the first to fourth nonwoven fabric layers together at the first joining part.

Heat-embossing patterns of the first joining part and the second joining part are not particularly limited. The first joining part and the second joining part may be disposed in a scattered point pattern in any shape or may be disposed in a lattice pattern or a linear pattern. In the case that the first joining part and the second joining part are disposed in a scattered point pattern, each single shape of the first joining part and the second joining part is not particularly limited and may be circular, elliptical, polygonal, wavy, starlike or the other. Arrangement patterns of the first joining part and the second joining part are not also particularly limited, and the first joining part and the second joining part may be provided in a regular pattern or in a random pattern. In the case that the first joining part and the second joining part are disposed in a lattice pattern or a linear pattern, each line constituting the lattice pattern or the linear pattern may be any form such as a straight line, a wavy line, a zigzag line or the like, and the each line is preferably provided over a substantially entire area of the nonwoven fabric layer in one direction or in both one direction and another direction in the plane. In any case, at least a portion of the second joining part is preferably provided at a region between the first joining parts, and thus, it is preferably provided that a region where the first joining part is provided is overlapped with a region where the second joining part is provided.

The first joining part is preferably disposed in a scattered point pattern. When the first joining part is disposed in a scattered point pattern, it is possible to decrease the heat-embossed area in the first nonwoven fabric layer, thereby improving hand feeling of the nonwoven fabric laminate. Moreover, by providing the first joining part in a scattered point pattern, the first nonwoven fabric layer can be formed so as to float to the second nonwoven fabric layer in more area, thereby improving the visual shielding property through the nonwoven fabric laminate. From the viewpoint of improving appearance of the nonwoven fabric laminate, it is preferred that a plurality of the first joining parts are aligned in both one direction and another direction in the nonwoven fabric laminate. Here, one direction and another direction in the nonwoven fabric laminate means one direction and another direction in a plane including the nonwoven fabric laminate.

The second joining part is preferably disposed in a scattered point pattern. When the second joining part is disposed in a scattered point pattern, it becomes easy to ensure flexibility of the nonwoven fabric laminate even though the second joining part is formed as well as the first joining part in the second nonwoven fabric layer and the third nonwoven fabric layer. As a result, even when the nonwoven fabric laminate is distorted in use, the nonwoven fabric laminate easily follows the distortion smoothly. From the viewpoint that the nonwoven fabric laminate easily deforms against an external force smoothly, it is preferred that a plurality of the second joining parts are aligned in both one direction and another direction in the nonwoven fabric laminate.

It is preferred that a plurality of the first joining parts are disposed so as to be aligned in one direction and another direction in the nonwoven fabric laminate, and a plurality of the second joining parts are disposed so as to be aligned in one direction and another direction in the nonwoven fabric laminate at a region except the first joining parts being disposed. When the first joining parts and the second joining parts are disposed in this manner, hand feeling of the nonwoven fabric laminate is improved and the nonwoven fabric laminate easily deforms against an external force smoothly. Moreover, the visual shielding property through the nonwoven fabric laminate is improved and the appearance of the nonwoven fabric laminate is also improved.

It is preferred that an area of the one (single) first joining part is larger than that of the one (single) second joining part. Thus, it is preferred that the first joining part is disposed in a shape that is larger than the second joining part. By providing the first joining part in this manner, each of the nonwoven fabric layers is firmly joined at the first joining part, thereby increasing integrity of the nonwoven fabric laminate.

It is preferred that a number of the second joining part is larger than that of the first joining part. When the second joining part is provided larger in number than the first joining part, the area where the second nonwoven fabric layer and the third nonwoven fabric layer are heat-embossed can be increased, whereby the strength of the nonwoven fabric laminate is enhanced. The numbers of the first joining parts and the second joining parts may be measured by counting numbers of the first joining parts and the second joining parts formed in a certain area (e.g., an area of 5 cm×5 cm). Further, the second joining part is preferably provided with a smaller shape and larger in number than the first joining part, and by providing the second joining part in this manner, it becomes easy to ensure the flexibility of the second nonwoven fabric layer and the third nonwoven fabric layer.

It is preferred that a total area of the first joining part is smaller than that of the second joining part. When the first joining part and the second joining part are provided in this manner, it becomes easy to improve hand feeling of the nonwoven fabric laminate while increasing strength of the nonwoven fabric laminate. The total area of the first joining part can be determined by measuring percentage of the embossed area by the first joining part in the first nonwoven fabric layer, and the total area of the second joining part can be determined by measuring percentage of the embossed area by the first joining part and the second joining part and subtracting the percentage of the embossed area by the first joining part therefrom.

The first joining part and the second joining part may have a same shape to each other or may have a different shape from each other. For example, both of the first joining part and the second joining part may be formed in a circular shape. In this case, it becomes easy to provide a desired physical property isotropically to the nonwoven fabric laminate.

Meanwhile, in the case where the first joining part and the second joining part are formed in a different shape from each other, it is possible, for example, to determine the shape of the first joining part from the viewpoint of ensuring the integrity of the nonwoven fabric laminate and determine the shape of the second joining part from the viewpoint of increasing the strength of the nonwoven fabric laminate. Thus, it becomes possible to give a desired physical property to the nonwoven fabric laminate in accordance with an actual usage. For example, in the case that the nonwoven fabric laminate tends to have a load in a specific direction in use, when the first joining part is formed in an elongated shape in the specific direction and the second joining part is formed in a circular shape, the integrity of the nonwoven fabric laminate can be ensured even in the state where the nonwoven fabric laminate have a load in the specific direction, and further, the strength of the entire nonwoven fabric laminate can be increased.

Types of a nonwoven fabric constituting each of the nonwoven fabric layer is not particularly limited, and a spunbonded nonwoven fabric, an air-through nonwoven fabric, a point-bonded nonwoven fabric, a meltblown nonwoven fabric, an air-laid nonwoven fabric or the like can be employed. In the case where the nonwoven fabric laminate is applied to, for example, absorbent articles, covers, bags, protective clothing and sheets as described above, the nonwoven fabric laminate preferably has breathability, and in this case, each of the nonwoven fabric layer is preferably made of a spunbonded nonwoven fabric or an air-through nonwoven fabric. When each of the nonwoven fabric layer is made of such nonwoven fabric, breathability of the nonwoven fabric laminate is increased and internal humidity is easily decreased.

As a specific constitution of the nonwoven fabric layers, it is preferred that each of the first nonwoven fabric layer, the second nonwoven fabric layer and the third nonwoven fabric layer is made of a spunbonded nonwoven fabric, for example. When the nonwoven fabric laminate is constituted in this manner, breathability of the nonwoven fabric laminate is increased, and further, since a spunbonded nonwoven fabric is able to be formed relatively thin, the nonwoven fabric layers can be firmly joined to each other by joining the first nonwoven fabric layer, the second nonwoven fabric layer and the third nonwoven fabric layer to each other at the first joining part by heat-embossing, whereby integrity of the nonwoven fabric laminate is enhanced. In this case, if the nonwoven fabric laminate comprises the fourth nonwoven fabric layer, the fourth nonwoven fabric layer is also preferably made of a spunbonded nonwoven fabric.

As a specific constitution of the nonwoven fabric layers, it is also preferred that the first nonwoven fabric layer is made of an air-through nonwoven fabric and the second and third nonwoven fabric layers are made of a spunbonded nonwoven fabric. An air-through nonwoven fabric is relatively bulky and has a good texture, and hence, when the first nonwoven fabric layer located on an outer surface of the nonwoven fabric laminate is made of an air-through nonwoven fabric, hand feeling of the nonwoven, fabric laminate is improved while increasing breathability of the nonwoven fabric laminate. In this case, if the nonwoven fabric laminate comprises the fourth nonwoven fabric layer, the fourth nonwoven fabric layer is preferably made of an air-through nonwoven fabric as well as the first nonwoven fabric layer.

A spunbonded nonwoven fabric and an air-through nonwoven fabric can be formed such that fibers constituting the nonwoven fabric orient in one direction. In the case that the first nonwoven fabric layer, the second nonwoven fabric layer and the third nonwoven fabric layer (or further the fourth nonwoven fabric layer) are made of a spunbonded nonwoven fabric or an air-through nonwoven fabric, the first joining part preferably has a shape that is shorter in an orientation direction of fibers constituting the nonwoven fabric than in its orthogonal direction. A nonwoven fabric in which constituent fibers are oriented in one direction is formed that breaking strength becomes weak with respect to a direction orthogonal to the orientation direction of the constituent fibers; however, when the first joining part is formed in a shape that is shorter in the fiber orientation direction of the nonwoven fabric (that is, longer in the direction orthogonal to the fiber orientation direction of the nonwoven fabric), the constituent fibers of the nonwoven fabric are firmly joined together by heat-embossing at the first joining part, whereby breaking strength of the nonwoven fabric can be increased. As a result, even when the nonwoven fabric laminate is stretched, integrity of the nonwoven fabric laminate is easily maintained. In this case, it is preferred that constituent fibers in all of the nonwoven fabric layers are oriented in the same direction.

The fiber orientation direction of a spunbonded nonwoven fabric or an air-through nonwoven fabric can be determined by observing a surface of the nonwoven fabric with a microscope or the like. A spunbonded nonwoven fabric is formed by, for example, melting a polymer material, extruding from a spinneret to be stretched, and collecting on a conveyer belt or the like to form a web; and on this occasion, the web (fibers) collected on the conveyer belt is arranged along a traveling direction of the conveyer belt. Therefore, in this case, the web (fibers) comes to be oriented in the traveling direction (MD direction) of the conveyer belt. In the air-through nonwoven fabric, the orientation direction of the constituent fibers can be arranged by appropriately setting a collection method of raw short fibers in forming a fiber aggregate or a fiber-opening method in forming a web, upon manufacturing the nonwoven fabric.

The second joining part also may be formed to have a shape that is shorter in the orientation direction of fibers constituting the nonwoven fabric than in its orthogonal direction. In this case, strength of the nonwoven fabric, with respect to the orthogonal direction to fiber orientation direction, of the second nonwoven fabric layer and the third nonwoven fabric layer can be further increased.

Regarding the first joining part and the second joining part, examples of the elongated shape in one direction include an ellipse shape, a rectangle shape, a rhombus shape, a wave shape, a radiation shape and the like. For example, in the case of an elliptical shape, it may be provided in the nonwoven fabric laminate so that the long axis direction corresponds to the one direction.

Fineness of each of the nonwoven fabric layers is not particularly limited; however, it is preferred that fineness of the first nonwoven fabric layer is larger than those of second nonwoven fabric layer and the third nonwoven fabric layer. In the case that the nonwoven fabric layer comprises the fourth nonwoven fabric layer, it is preferred that fineness of the fourth nonwoven fabric layer is also larger than those of the second nonwoven fabric layer and the third nonwoven fabric layer. When the first nonwoven fabric layer or the fourth nonwoven fabric layer is formed in this manner, void ratio of the first nonwoven fabric layer or the fourth nonwoven fabric layer tends to increase and the first nonwoven fabric layer or the fourth nonwoven fabric layer is formed bulky, resulting in easily improving hand feeling of the nonwoven fabric laminate.

Examples of the nonwoven fabric laminate is described below, referring to FIGS. 1 and 2. However, the nonwoven fabric laminate of the present invention is not limited to the embodiments shown in the drawings.

FIG. 1 shows a perspective view of a nonwoven fabric laminate in which the first nonwoven fabric layer, the second nonwoven fabric layer and the third nonwoven fabric layer are laminated. A nonwoven fabric laminate 1 shown in FIG. 1 comprises a first nonwoven fabric layer 2, a second nonwoven fabric layer 3 and a third nonwoven fabric layer 4, and the first nonwoven fabric layer 2, the second nonwoven fabric layer 3 and the third nonwoven fabric layer 4 are laminated in this order. In the nonwoven fabric laminate 1, the first nonwoven fabric layer 2 forms a surface which a user mainly touches by hand.

The first nonwoven fabric layer 2, the second nonwoven fabric layer 3 and the third nonwoven fabric layer 4 are joined to each other at first joining parts 6 by heat-embossing, and the second nonwoven fabric layer 3 and the third nonwoven fabric layer 4 are further joined to each other at second joining parts 7 by heat-embossing. In the nonwoven fabric laminate 1, as the nonwoven fabric layers are joined together in this manner, strength of the nonwoven fabric laminate 1 can be increased by the heat-embossed first and second joining parts 6,7, while hand feeling of the first nonwoven fabric layer 2 side of the nonwoven fabric laminate 1 can be improved since the first nonwoven fabric layer 2 is heat-embossed only at the first joining parts 6. Further, the nonwoven fabric laminate 1 is configured such that the joining pattern of the first nonwoven fabric layer 2 with the second nonwoven fabric layer 3 is different from the joining pattern of the second nonwoven fabric layer 3 with the third nonwoven fabric layer 4, and therefore, interlayer distances between the respective nonwoven fabric layers are variously changed, whereby a visual shielding property of the nonwoven fabric laminate 1 can be increased.

It is preferred that the first joining parts 6 and the second joining parts 7 are respectively arranged in a matrix in a plane, as shown in FIG. 1. That is, it is preferred that a plurality of the first joining parts 6 are disposed so as to be aligned in one direction and another direction in the nonwoven fabric laminate 1, and a plurality of the second joining parts 7 are disposed so as to be aligned in one direction and another direction in the nonwoven fabric laminate 1 at a region except the first joining parts 6 being formed. When the first joining parts 6 and the second joining parts 7 are formed in this manner, the visual shielding property of the nonwoven fabric laminate 1 is increased and the appearance of the nonwoven fabric laminate 1 is improved, as well as hand feeling of the nonwoven fabric laminate 1 is enhanced. In addition, the nonwoven fabric laminate 1 comes to easily deform against an external force smoothly, thereby improving handleability of the nonwoven fabric laminate 1.

The first joining part 6 and the second joining part 7 are preferably formed as follows. That is, the first joining parts 6 are preferably formed such that an area of the one first joining part 6 is larger than that of the one second joining part 7. Meanwhile, it is preferred that a total area of the first joining parts 6 is smaller than that of the second joining parts 7. Therefore, it is preferred that a number of the second joining part 7 is larger than that of the first joining part 6.

In FIG. 1, the first joining part 6 and the second joining part 7 have a same shape (a circular shape) to each other; however, the first joining part 6 and the second joining part 7 may have a different shape from each other. Also in FIG. 1, the first joining parts 6 are formed in a uniform shape and the second joining parts 7 are formed in a uniform shape; however, the first joining parts 6 may be formed in a plurality of various shapes and the second joining parts 7 may be also formed in a plurality of various shapes. Alternatively, the first joining part 6 and the second joining part 7 may be formed in a lattice shape or a linear shape (for example, a wavy shape or a zigzag line shape).

FIG. 2 shows a perspective view of a nonwoven fabric laminate in which the first nonwoven fabric layer, the second nonwoven fabric layer, the third nonwoven fabric layer and the fourth nonwoven fabric layer. In the explanation of the nonwoven fabric laminate shown in FIG. 2, explanations overlapping the above description regarding the FIG. 1 are omitted.

A nonwoven fabric laminate 1 shown in FIG. 2 comprises a first nonwoven fabric layer 2, a second nonwoven fabric layer 3, a third nonwoven fabric layer 4 and a fourth nonwoven fabric layer 5, and the first nonwoven fabric layer 2, the second nonwoven fabric layer 3, the third nonwoven fabric layer 4 and the fourth nonwoven fabric layer 5 are laminated in this order. The first nonwoven fabric layer 2, the second nonwoven fabric layer 3, the third nonwoven fabric layer 4 and the fourth nonwoven fabric layer 5 are joined to each other at first joining parts 6 by heat-embossing, and the second nonwoven fabric layer 3 and the third nonwoven fabric layer 4 are further joined to each other at second joining parts 7 by heat-embossing. In the nonwoven fabric laminate 1, as the nonwoven fabric layers are joined together in this manner, strength of the nonwoven fabric laminate 1 is increased by the heat-embossed first and second joining parts 6,7, while hand feeling of both the first nonwoven fabric layer 2 side and the fourth nonwoven fabric layer 5 side of the nonwoven fabric laminate 1 can be improved since the first nonwoven fabric layer 2 and the fourth nonwoven fabric layer 5 are heat-embossed only at the first joining parts 6.

[Process for Producing Nonwoven Fabric Laminate]

Next, a process for producing the nonwoven fabric laminate of the present invention is explained. A process for producing a nonwoven fabric laminate comprises the steps in the sequence set forth: forming a third nonwoven fabric layer (a third nonwoven fabric layer-forming step); forming a second nonwoven fabric layer on the third nonwoven fabric layer (a second nonwoven fabric layer-forming step); heat-embossing the second nonwoven fabric layer and the third nonwoven fabric layer to join to each other at a second joining part (a second joining part-forming step); forming a first nonwoven fabric layer on the second nonwoven fabric layer (a first nonwoven fabric layer-forming step); and heat-embossing the first nonwoven fabric layer, the second nonwoven fabric layer and the third nonwoven fabric layer to join to each other at a first joining part (a first joining part-forming step). According to the process for producing a nonwoven fabric laminate of the present invention, the nonwoven fabric laminate of the present invention can be easily manufactured.

In the third nonwoven fabric layer-forming step, the third nonwoven fabric layer is formed by using a conventionally-known method depending on the type of the nonwoven fabric constituting the third nonwoven fabric layer.

In the second nonwoven fabric layer-forming step, the second nonwoven fabric layer is formed on the third nonwoven fabric layer by using a conventionally-known method depending on the type of the nonwoven fabric constituting the second nonwoven fabric layer. The second nonwoven fabric layer is formed on one surface of the third nonwoven fabric layer. In the second nonwoven fabric layer-forming step, the second nonwoven fabric layer which was already formed in a layer may be stacked on the third nonwoven fabric layer, or the second nonwoven fabric layer may be formed in a layer on the third nonwoven fabric layer. For example, in the case where the second nonwoven fabric layer is made of a spunbonded nonwoven fabric or a meltblown nonwoven fabric, the second nonwoven fabric layer can be formed directly on the third nonwoven fabric layer by the latter method, that is, collecting melted fibers onto the third nonwoven fabric layer.

In the second joining part-forming step, the second nonwoven fabric layer and the third nonwoven fabric layer are heat-embossed in a stacked state to be joined to each other. By heat-embossing the second nonwoven fabric layer and the third nonwoven fabric layer, a second joining part where the heat-emboss was applied is formed and the second nonwoven fabric layer and the third nonwoven fabric layer are joined to each other at the second joining part. The heat-emboss can be formed by inserting the second nonwoven fabric layer and the third nonwoven fabric layer in the stacked state between two rolls to be conveyed, and on this occasion, a heat-embossing roll (that is a roll having a predetermined embossed pattern on its surface and being heatable) may be used for at least one of the rolls. Alternatively, heat-embossing can be also conducted by bringing a ultrasonic transducer contact with the second nonwoven fabric layer and the third nonwoven fabric layer of the stacked state and pressurizing.

In the first nonwoven fabric layer-forming step, the first nonwoven fabric layer is formed on the second nonwoven fabric layer by using a conventionally-known method depending on the type of the nonwoven fabric constituting the first nonwoven fabric layer. The first nonwoven fabric layer is formed on one surface of the second nonwoven fabric layer (that is the surface opposite to the third nonwoven fabric layer). In the first nonwoven fabric layer-forming step, the first nonwoven fabric layer which was already formed in a layer may be stacked on the second nonwoven fabric layer, or the first nonwoven fabric layer may be formed in a layer on the second nonwoven fabric layer. For example, in the case where the first nonwoven fabric layer is made of a spunbonded nonwoven fabric or a meltblown nonwoven fabric, the first nonwoven fabric layer can be formed directly on the second nonwoven fabric layer by the latter method, that is, collecting melted fibers onto the second nonwoven fabric layer. By conducting the first nonwoven fabric layer-forming step, the first nonwoven fabric layer is formed on the laminate of the second nonwoven fabric layer and the third nonwoven fabric layer.

In the first joining part-forming step, the first nonwoven fabric layer, the second nonwoven fabric layer and the third nonwoven fabric layer are heat-embossed collectively in a stacked state to be joined to each other. By heat-embossing the first nonwoven fabric layer, the second nonwoven fabric layer and the third nonwoven fabric layer, a first joining part is formed at a part where the heat-emboss was applied and the first nonwoven fabric layer, the second nonwoven fabric layer and the third nonwoven fabric layer are joined to each other at the first joining part. By conducting the first joining part-forming step, the nonwoven fabric laminate in which the first nonwoven fabric layer, the second nonwoven fabric layer and the third nonwoven fabric layer are joined to each other at the first joining part and the second joining part. The first joining part is formed so as not to overlap with at least a portion of the second joining part. The first joining part can be formed by using a heat-embossing roll, as with the second joining part.

In the case of producing the nonwoven fabric laminate comprising the fourth nonwoven fabric layer in the production process of the present invention, it is preferred that the fourth nonwoven fabric layer is formed under the third nonwoven fabric layer as well as the first nonwoven fabric layer is formed on the second nonwoven fabric layer in the first nonwoven fabric layer-forming step. This step is referred to as a first and fourth nonwoven fabric layers forming step.

In the first and fourth nonwoven fabric layers forming step, the first nonwoven fabric layer is formed on the second nonwoven fabric layer as described above. Thus, the first nonwoven fabric layer is formed on one surface of the second nonwoven fabric layer (that is the surface opposite to the third nonwoven fabric layer). The fourth nonwoven fabric layer is formed by using a conventionally-known method depending on the type of the nonwoven fabric constituting the fourth nonwoven fabric layer. The fourth nonwoven fabric layer is formed on the other surface of the third nonwoven fabric layer (that is the surface opposite to the second nonwoven fabric layer). In the first and fourth nonwoven fabric layers forming step, the fourth nonwoven fabric layer which was already formed in a layer may be disposed under the third nonwoven fabric layer, or the fourth nonwoven fabric layer may be formed in a layer on the third nonwoven fabric layer of the laminate comprising the second nonwoven fabric layer and the third nonwoven fabric layer (and may further comprise the first nonwoven fabric layer), that is disposed in the state where the third nonwoven fabric layer is placed at the top side. For example, in the case where the fourth nonwoven fabric layer is made of a spunbonded nonwoven fabric or a meltblown nonwoven fabric, the fourth nonwoven fabric layer can be formed directly on the third nonwoven fabric layer by the latter method, that is, collecting melted fibers onto the third nonwoven fabric layer. By conducting the first and fourth nonwoven fabric layers forming step, the first nonwoven fabric layer is formed on the laminate of the second nonwoven fabric layer and the third nonwoven fabric layer and the fourth nonwoven fabric layer is formed under the laminate of the second nonwoven fabric layer and the third nonwoven fabric layer. In the first and fourth nonwoven fabric layers forming step, the order of forming the first nonwoven fabric layer and the fourth nonwoven fabric layer is not particularly limited.

The first joining part-forming step is conducted, following the first and fourth nonwoven fabric layers forming step. In the first joining part-forming step, the first nonwoven fabric layer, the second nonwoven fabric layer, the third nonwoven fabric layer and the fourth nonwoven fabric layer are heat-embossed collectively in a stacked state to be joined to each other. By heat-embossing the first nonwoven fabric layer, the second nonwoven fabric layer, the third nonwoven fabric layer and the fourth nonwoven fabric layer, a first joining part is formed at a part where the heat-emboss was applied and the first nonwoven fabric layer, the second nonwoven fabric layer, the third nonwoven fabric layer and the fourth nonwoven fabric layer are joined to each other at the first joining part. By conducting the first joining part-forming step, the nonwoven fabric laminate in which the first nonwoven fabric layer, the second nonwoven fabric layer, the third nonwoven fabric layer and the fourth nonwoven fabric layer are joined to each other at the first joining part and the second joining part. The first joining part is formed so as not to overlap with at least a portion of the second joining part. The first joining part can be formed by using a heat-embossing roll, as with the second joining part.

If the nonwoven fabric laminate obtained as described above is a continuous body, the continuous body may be cut into an individual nonwoven fabric laminate. Alternatively, the continuous body of the nonwoven fabric laminate may be supplied to the subsequent manufacturing process to, continuously produce nonwoven products (e.g., absorbent articles or the like).

In the process for producing the nonwoven fabric laminate of the present invention, the first nonwoven fabric layer, the second nonwoven fabric layer and the third nonwoven fabric layer are preferably made of a spunbonded nonwoven fabric or a meltblown nonwoven fabric. In the case where the nonwoven fabric laminate comprises the fourth nonwoven fabric layer, the fourth nonwoven fabric layer is also preferably made of a spunbonded nonwoven fabric or a meltblown nonwoven fabric. In this case, all of the nonwoven fabric layers may be spunbonded nonwoven fabrics or meltblown nonwoven fabrics, or a part of the nonwoven fabric layers may be a spunbonded nonwoven fabric and the other part of the nonwoven fabric layers may be a meltblown nonwoven fabric. When the first nonwoven fabric layer, the second nonwoven fabric layer and the third nonwoven fabric layer are made of a spunbonded nonwoven fabric or a meltblown nonwoven fabric, the second nonwoven fabric layer (or the first nonwoven fabric layer) can be formed into a web directly on the third nonwoven fabric layer (or the second nonwoven fabric layer), and so the nonwoven fabric laminate can be easily manufactured. Further, when the fourth nonwoven fabric layer is made of a spunbonded nonwoven fabric or a meltblown nonwoven fabric, the fourth nonwoven fabric layer can be formed into a web directly on the third nonwoven fabric layer, and so the nonwoven fabric laminate can be easily manufactured. In the case that the nonwoven fabric laminate is applied to an exterior sheet of an absorbent article as described below, the first nonwoven fabric layer, the second nonwoven fabric layer and the third nonwoven fabric layer are preferably made of a spunbonded nonwoven fabric.

Preferred embodiments relating to the shapes and arrangements of the first joining part and the second joining part are the same as described above. For example, it is preferred that a plurality of the first joining parts or the second joining parts are disposed so as to be aligned in one direction and another direction, and it is preferred that an area of the one (single) first joining part is larger than that of the one (single) second joining part or a number of the second joining part is larger than that of the first joining part, and the first joining part and the second joining part may have a different shape from each other. In the case where the first nonwoven fabric layer, the second nonwoven fabric layer and the third nonwoven fabric layer are made of a spunbonded nonwoven fabric, the first joining part is preferably formed to have a shape that is shorter in the fiber orientation direction of the nonwoven fabric than in its orthogonal direction. The second joining part may be formed in this manner.

The nonwoven fabric laminate of the present invention may be obtained by the above production process, that is, it comprises the first nonwoven fabric layer, the second nonwoven fabric layer and the third nonwoven fabric layer, and may be obtained by a process for producing a nonwoven fabric laminate comprising the steps in the sequence set forth: forming the second nonwoven fabric layer on the third nonwoven fabric layer; heat-embossing the second nonwoven fabric layer and the third nonwoven fabric layer to join to each other at the second joining part; forming the first nonwoven fabric layer on the second nonwoven fabric layer; and heat-embossing the first nonwoven fabric layer, the second nonwoven fabric layer and the third nonwoven fabric layer to join to each other at the first joining part. Or, the nonwoven fabric laminate of the present invention comprises the first nonwoven fabric layer, the second nonwoven fabric layer, the third nonwoven fabric layer and the fourth nonwoven fabric layer, and may be obtained by a process for producing a nonwoven fabric laminate comprising the steps in the sequence set forth: forming the second nonwoven fabric layer on the third nonwoven fabric layer; heat-embossing the second nonwoven fabric layer and the third nonwoven fabric layer to join to each other at the second joining part; forming the first nonwoven fabric layer on the second nonwoven fabric layer and the fourth nonwoven fabric layer under the third nonwoven fabric layer; and heat-embossing the first nonwoven fabric layer, the second nonwoven fabric layer, the third nonwoven fabric layer and the fourth nonwoven fabric layer to join to each other at the first joining part. Details of each step are the same as described above.

An example of the process for producing a nonwoven fabric laminate of the present invention is described below, referring to FIG. 3. FIG. 3 shows a schematic view of a process for producing the nonwoven fabric laminate in which the first nonwoven fabric layer, the second nonwoven fabric layer and the third nonwoven fabric layer are made of a spunbonded nonwoven fabric.

In the third nonwoven fabric layer-forming step 61, the third nonwoven fabric layer 43 is formed. In FIG. 3, plural rows of a molten polymer material are continuously fed from a fiber supply device 42 and collected on a conveyer belt 41 conveyed in the direction w, thereby forming the third nonwoven fabric layer 43 of a spunbonded nonwoven fabric.

In the second nonwoven fabric layer-forming step 62, the second nonwoven fabric layer 45 is formed on the third nonwoven fabric layer 43. In FIG. 3, plural rows of a molten polymer material are continuously fed from a fiber supply device 44 and collected on the third nonwoven fabric layer 43 conveyed in the direction w, thereby forming the second nonwoven fabric layer 45 of a spunbonded nonwoven fabric on the third nonwoven fabric layer 43.

In the second joining part-forming step 63, the second nonwoven fabric layer 45 and the third nonwoven fabric layer 43 are heat-embossed to be joined to each other at second joining parts. In FIG. 3, the second nonwoven fabric layer 45 and the third nonwoven fabric layer 43 in a stacked state are inserted between a heat-embossing roll 46 and a flat roll 47, thereby joining the second nonwoven fabric layer 45 and the third nonwoven fabric layer 43 to each other by heat-embossing. A predetermined embossing pattern is formed on the surface of the heat-embossing roll 46, and the second nonwoven fabric layer 45 and the third nonwoven fabric layer 43 are joined to each other at the second joining part formed in that pattern.

In the first nonwoven fabric layer-forming step 64, the first nonwoven fabric layer 49 is formed on the second nonwoven fabric layer 45. In FIG. 3, plural rows of a molten polymer material are continuously fed from a fiber supply device 48 and collected on the laminate of the third nonwoven fabric layer 43 and the second nonwoven fabric layer 45 conveyed in the direction w, thereby forming the first nonwoven fabric layer 49 of a spunbonded nonwoven fabric on the second nonwoven fabric layer 45.

In the first joining part-forming step 65, the first nonwoven fabric layer 49, the second nonwoven fabric layer 45 and the third nonwoven fabric layer 43 are heat-embossed to be joined to each other at first joining parts. In FIG. 3, the first nonwoven fabric layer 49, the second nonwoven fabric layer 45 and the third nonwoven fabric layer 43 in a stacked state are inserted between a heat-embossing roll 50 and a flat roll 51, thereby joining the first nonwoven fabric layer 49, the second nonwoven fabric layer 45 and the third nonwoven fabric layer 43 to each other by heat-embossing. A predetermined embossing pattern is formed on the surface of the heat-embossing roll 50, and the first nonwoven fabric layer 49, the second nonwoven fabric layer 45 and the third nonwoven fabric layer 43 are joined to each other at the first joining part formed in that pattern. As a result, the nonwoven fabric laminate 52 (a continuous body) in which the first nonwoven fabric layer 49, the second nonwoven fabric layer 45 and the third nonwoven fabric layer 43 are integrally joined to each other at the first and second joining parts is obtained.

[Absorbent Article]

Next, an absorbent article of the present invention is explained. An absorbent article of the present invention comprises an exterior sheet formed of the nonwoven fabric laminate of the present invention. By employing the nonwoven fabric laminate of the present invention for the exterior sheet of an absorbent article, hand feeling of the exterior sheet can be improved while strength thereof is increased. Examples of the absorbent article include a disposable diaper, an incontinence pad (including a light incontinence pad) and a sanitary napkin.

The absorbent article has a skin-facing side and an outer side with respect to a thickness direction of the absorbent article. A skin-facing side of the absorbent article means a side close to wearer's skin in wearing the absorbent article and an outer side of the absorbent article means a side opposite to a wearer in wearing the absorbent article.

The exterior sheet is located on an outer side of the absorbent article. For example, the absorbent article comprises a top sheet, a back sheet and an absorbent core provided therebetween, and in the case where the back sheet is disposed on an outer side of the absorbent article, the back sheet corresponds to the exterior sheet. In the case where the absorbent article is a pants-type disposable diaper, the pants-type disposable diaper may be formed such that an absorbent body comprising a top sheet, a back sheet and an absorbent core provided therebetween is disposed on a skin-facing side of a pants member that is formed in a pants shape; and in this case, at least a portion of the pants member may be composed of the exterior sheet. As just described, it is preferred that the exterior sheet is provided so as to constitute the outer side the absorbent article.

A shape of the absorbent article is not particularly limited. In the case where the absorbent article is an incontinence pad, examples of the shape of the absorbent article include a substantially rectangular shape, an hourglass shape, a center nipped-in gourd shape, a battledore shape and others.

In the case where the absorbent article is a disposable diaper, the absorbent article has, for example, a front part, a rear part, and a crotch part positioned therebetween and provided with an absorbent core. The disposable diaper may be an open-type (tape-type) disposable diaper that is provided with a pair of fastening members on left and right sides of a rear part and is formed into a pants shape by using the fastening members in wearing, or the disposable diaper may be a pants-type disposable diaper that is formed in a pants shape and has a waist opening and a pair of leg openings. The disposable diaper may comprise, for example, an exterior member having a front part, a rear part and a crotch part positioned therebetween and an absorbent body comprising a top sheet, a back sheet and an absorbent core provided therebetween, wherein the absorbent body is disposed on a skin-facing side of the exterior member. Or, the disposable diaper may be formed such that a laminate comprising a top sheet, a back sheet and an absorbent core provided therebetween has a front part, a rear part and a crotch part positioned therebetween. Here, the front part means a part applied to an abdomen side of the wearer, the rear part means a part applied to a back side of the wearer, and the crotch part means a part positioned between the front part and the rear part and applied to a crotch of the wearer, in wearing the disposable diaper.

The exterior sheet is composed of the nonwoven fabric laminate of the present invention. In the nonwoven fabric laminate of the present invention, the first nonwoven fabric layer is preferably a surface which a user mainly touches by hand; and therefore, in the case of applying to the exterior sheet of the absorbent article, the first nonwoven fabric layer preferably located on an outer side of the absorbent article. Thus, it is preferred that the exterior sheet comprises the first nonwoven fabric layer, the second nonwoven fabric layer and the third nonwoven fabric layer from the outer side of the absorbent article, the first nonwoven fabric layer, the second nonwoven fabric layer and the third nonwoven fabric layer are joined to each other at the first joining part by heat-embossing, and the second nonwoven fabric layer and the third nonwoven fabric layer are further joined to each other at the second joining part by heat-embossing.

Since the exterior sheet is constituted in this manner, both strength and hand feeling can be enhanced. That is, in the exterior sheet, the second nonwoven fabric layer and the third nonwoven fabric layer, that are located close to the skin-facing side, are joined to each other at both the first joining part and the second joining part by heat-embossing, whereby strength of the exterior sheet can be increased. And, the first nonwoven fabric layer is provided on the outer side of the second sheet and is joined to the second nonwoven fabric layer only at the first joining part, whereby joining parts formed by heat-embossing are decreased and hand feeling of the exterior sheet located on the outer side of the absorbent article can be made good. In addition, since the exterior sheet is formed such that the joining pattern of the first nonwoven fabric layer with the second nonwoven fabric layer is different from the joining pattern of the second nonwoven fabric layer with the third nonwoven fabric layer, interlayer distances between the nonwoven fabric layers are variously changed, that makes degree of transmission or diffusion of light through the exterior sheet uneven properly, whereby a visual shielding property through the exterior sheet can be increased. For example, in the case that an elastic member is disposed to the skin-facing side of the exterior sheet, the elastic member becomes hardly seen from the outside of the absorbent article, or in the case that an absorbent core disposed to the skin-facing side of the exterior sheet is colored by absorbing excrement, the absorbent core can be made less obvious seen from the outside of the absorbent article.

The exterior sheet is formed by laminating the first nonwoven fabric layer, the second nonwoven fabric layer and the third nonwoven fabric layer and is handled as a single sheet member; and thus, no elastic member is provided between the respective nonwoven fabric layers constituting the exterior sheet (that is, between the first nonwoven fabric layer and the second nonwoven fabric layer, and between the second nonwoven fabric layer and the third nonwoven fabric layer). In the exterior sheet, another layer may be provided on the outer side of the first nonwoven fabric layer or the skin-facing side of the third nonwoven fabric layer; however, the exterior sheet preferably does not comprise so many layers in view of easily ensuring flexibility and breathability of the exterior sheet and preferably consists of the first nonwoven fabric layer, the second nonwoven fabric layer and the third nonwoven fabric layer.

Preferred embodiments relating to the arrangement patterns, shapes, sizes and the like of the first joining part and the second joining part are the same as described above. For example, it is preferred that a plurality of the first joining parts are disposed so as to be aligned in one direction and another direction in the exterior sheet, and a plurality of the second joining parts are disposed so as to be aligned in one direction and another direction in the exterior sheet at a region except the first joining parts being disposed. When the first joining parts and the second joining parts are disposed in such a manner, hand feeling of the exterior sheet is improved, and the exterior sheet easily deforms against an external force smoothly, that improves wearing feeling of the absorbent article. In addition, the visual shielding property through the exterior sheet is increased and the appearance of the absorbent article is also improved.

Types of a nonwoven fabric constituting each of the nonwoven fabric layer is not particularly limited, and a spunbonded nonwoven fabric, an air-through nonwoven fabric, a point-bonded nonwoven fabric, a meltblown nonwoven fabric, an air-laid nonwoven fabric or the like can be employed. Here, the exterior sheet is located on the outer side of the absorbent article and preferably has breathability, and in this respect, each of the nonwoven fabric layers constituting the exterior sheet is preferably made of a spunbonded nonwoven fabric or an air-through nonwoven fabric. When each of the nonwoven fabric layers of the exterior sheet is made of such nonwoven fabric, breathability of the exterior sheet is increased and internal humidity is easily decreased in wearing the absorbent article.

As a specific constitution of the first nonwoven fabric layer, the second nonwoven fabric layer and the third nonwoven fabric layer constituting the exterior sheet, it is preferred that each of the first nonwoven fabric layer, the second nonwoven fabric layer and the third nonwoven fabric layer is made of a spunbonded nonwoven fabric. When the exterior sheet is constituted in this manner, breathability of the exterior sheet is increased, and further, since a spunbonded nonwoven fabric is able to be formed relatively thin, the nonwoven fabric layers can be firmly joined to each other by joining the first nonwoven fabric layer, the second nonwoven fabric layer and the third nonwoven fabric layer to each other at the first joining part by heat-embossing, whereby integrity of the exterior sheet is enhanced.

Regarding the first nonwoven fabric layer, the second nonwoven fabric layer and the third nonwoven fabric layer, it is also preferred that the first nonwoven fabric layer is made of an air-through nonwoven fabric and the second and third nonwoven fabric layers are made of a spunbonded nonwoven fabric. An air-through nonwoven fabric is relatively bulky and has a good texture, and hence, when the first nonwoven fabric layer located on the outer side of the exterior sheet is made of an air-through nonwoven fabric, hand feeling of the exterior sheet is improved while increasing breathability of the exterior sheet.

In the case that an elastic member is disposed to the skin-facing side of the exterior sheet, the visual shielding property of the exterior sheet can be increased by providing the first joining part as follows, whereby the elastic member becomes hardly seen from the outside of the exterior sheet. That is, it is preferred that an elastic member is disposed to the skin-facing side of the exterior sheet and the first joining part has a shape that is shorter in an extending direction of the elastic member than in an orthogonal direction thereof. When the first joining part is provided in this manner, many wrinkles extending in the direction orthogonal to the extending direction of the elastic member are easily formed in the exterior sheet, and the elastic member becomes hardly seen from the outside of the exterior sheet. Specifically, in the present invention, two kinds of joining parts, the first joining part and the second joining part, are formed in the exterior sheet as described above, and therefore, a large number of fine wrinkles are formed in the exterior sheet and interlayer distances between the respective nonwoven fabric layers are randomly changed, thereby increasing the visual shielding effect of the exterior sheet.

In the case that an elastic member is disposed to the skin-facing side of the exterior sheet, it is also preferable that a plurality of the first joining parts are aligned in the extending direction of the elastic member and an orthogonal direction thereof, and a distance between the first joining parts in the extending direction of the elastic member is wider than that in the orthogonal direction thereof. Also in the case that the first joining part is provided in this manner, many wrinkles extending in the direction orthogonal to the extending direction of the elastic member tend to be formed in the exterior sheet when the elastic member disposed to the skin-facing side of the exterior sheet contracts, and as a result, the elastic member becomes hardly seen from the outside of the exterior sheet.

In the case that the elastic member is disposed to the skin-facing side of the exterior sheet, the elastic member is preferably adhered to the skin-facing side of the exterior sheet. In addition, the first joining part is preferably provided at a region where the elastic member is disposed in the exterior sheet.

Next, examples of the absorbent article of the present invention is explained, referring to drawings. However, the absorbent article of the present invention is not limited to the embodiments shown in the drawings.

FIGS. 4 and 5 show an example of the absorbent article of the present invention that is applied to an incontinence pad. FIG. 4 shows a plan view of a skin-facing side of an incontinence pad, and FIG. 5 shows a cross-sectional view along a line V-V of the incontinence pad shown in FIG. 4. In the drawings, an arrow x represents a width direction and an arrow y represents a longitudinal direction, and a direction orthogonal to the arrows x and y represents a thickness direction z. The longitudinal direction y corresponds to a direction extending in a front-rear direction at a crotch of a wearer when the wearer wears the absorbent article, and the width direction x means a direction orthogonal to the longitudinal direction y on the same plane as the absorbent article.

An absorbent article (an incontinence pad) 11 comprises a top sheet 12, a back sheet 13 and an absorbent core 14 provided therebetween. The top sheet 12 is located on a skin-facing side of the absorbent article 11 and allows urine and the like excreted from a wearer to permeate through. The urine and the like which has passed through the top sheet 12 is accommodated in the absorbent core 14. The back sheet 13 is located on an outer side of the absorbent article 11 and prevents the excrement from permeating outside. In the absorbent article 11, the absorbent core 14 is formed in an hourglass shape.

In the absorbent article 11, it is preferred that side sheets 15 extending in the longitudinal direction y are disposed on both sides of the top sheet 12 in the width direction x. The side sheet 15 is provided with a rising elastic member 16 at an inner part thereof in the width direction x, and the inner part of the side sheet 15 rises toward wearer's skin by contractive force of the rising elastic member 16 in using the absorbent article 11, thereby, preventing leakage of excrement such as urine and the like.

In the absorbent article 11, the nonwoven fabric laminate of the present invention can be used for the back sheet 13 as the exterior sheet. For example, in the case of using the nonwoven fabric laminate 1 shown in FIG. 1, the nonwoven fabric laminate 1 may be disposed such that the first nonwoven fabric layer 2 is located on the outer side of the absorbent article 11. By applying the nonwoven fabric laminate of the present invention to the back sheet 13 as the exterior sheet, hand feeling of the absorbent article 11 is improved and the appearance of the absorbent article 11 seen from the back sheet 13 side is enhanced, for example in the case of using the absorbent article 11 to be attached to an inner side of an underwear (pants). Moreover strength of the back sheet 13 can be ensured. Or, the nonwoven fabric laminate of the present invention may be further provided on the outer side of the back sheet 13 as the exterior sheet.

An another example of the absorbent article of the present invention is explained. FIGS. 6 to 8 show an example of the absorbent article that is applied to a pants-type disposable diaper. FIG. 6 shows a perspective view of a pants-type disposable diaper, FIG. 7 shows a plan view of the pants-type disposable diaper shown in FIG. 6 in a developed state where a front part and a rear part are disjoined, and FIG. 8 shows a cross-sectional view along a line VIII-VIII of the pants-type disposable diaper shown in FIG. 7.

An absorbent article (a pants-type disposable diaper) 21 comprises a pants member 24 having a waist opening 22 and a pair of leg openings 23, and an absorbent body 27 disposed on a skin-facing side of the pants member 24. The pants member 24 has a front part P, a rear part Q and a crotch part R positioned therebetween, and formed into a pants shape by joining the front part P and the rear part Q. In the absorbent article (a pants-type disposable diaper) 21, the front part P and the rear part Q constitute a body circumference part of the diaper, and a part between an edge of the waist opening 22 and an edge of the leg opening 23 corresponds to the body circumference part of the diaper.

In the absorbent article 21, the nonwoven fabric laminate of the present invention can be used for a sheet member located on the outer side of the pants member 24. In FIGS. 6 to 8, the nonwoven fabric laminate of the present invention is used for an exterior sheet 25 located on the outer side of the pants member 24, and an inner sheet 26 is laminated on the skin-facing side of the exterior sheet 25. By providing the exterior sheet 25 located on the outer side of the absorbent article 21, strength of the pants member 24 can be ensured while improving the hand feeling and appearance of the absorbent article 21.

The absorbent body 27 is disposed on the skin-facing side of the pants member 24 at least at the crotch part R, and comprises a top sheet 28, a back sheet 29 and an absorbent core 30 provided therebetween (see FIGS. 7 and 8). In the absorbent article 21, the absorbent body 27 and the absorbent core 30 are formed in a substantially rectangular shape. The back sheet 29 is folded along an edge of the absorbent core 30 in the width direction x and joined to the top sheet 28.

The absorbent body 27 is provided with rising flaps 31 on both sides thereof in the width direction x (see FIGS. 7 and 8). The rising flap 31 enables preventing leakage of excrement such as urine and the like. The rising flap 31 is preferably liquid-impermeable. The rising flap 31 is provided with a rising elastic member 32 at an upper end part thereof in its standing state (an end part of a wearer's side), and the rising flap 31 is promoted to stand by contractive force of the rising elastic member 32.

A plurality of waist elastic members 33 are disposed along an edge of the waist opening 22 at an end part, with respect to the longitudinal direction y, of the pants member 24. A waist-gather around a wearer's waist is formed by the waist elastic member 33, thereby preventing excrement such as urine and the like from leaking from a back side or an abdomen side.

A plurality of body elastic members 34 extending in the width direction x are disposed at the front part P and the rear part Q of the pants member 24. The body elastic members 34 are arranged at wider intervals than the waist elastic member 33. The body elastic member 34 functions to improve fittability around a wearer's body.

Leg elastic members 35, 36 are disposed in the pants member 24 along an edge of the leg opening 23. The leg elastic member consists of a front leg elastic member 35 disposed along a front side of the edge of the leg opening 23 and a rear leg elastic member 36 disposed along a rear side of the edge of the leg opening 23; and by the front leg elastic member 35 and the rear leg elastic member 36, the leg elastic member is disposed along almost the entire circumference of the edge of the leg opening 23. Leg-gathers around wearer's legs formed by the leg elastic members 35, 36 prevents excrement such as urine and the like from leaking from a crotch.

The waist elastic member 33, the body elastic member 34 and the leg elastic members 35, 36 may be disposed between the exterior sheet 25 and the inner sheet 26. Each of the elastic member is preferably bonded to the exterior sheet 25 and/or the inner sheet 26 in the stretched state. The exterior sheet 25 may be folded back at the edge of the waist opening 22 of the pants member 24 toward the inner sheet 26, and the waist elastic member 33 may be interposed between the folded and unfolded parts of the exterior sheet 25 and bonded to the exterior sheet 25.

In the case that an elastic member extending in the width direction x, such as the waist elastic member 33 and the body elastic member 34, is disposed between the exterior sheet 25 and the inner sheet 26, the first joining part provided in the exterior sheet 25 is preferably formed so as to have a shape that is longer in the longitudinal direction y than in the width direction x at the body circumference part of the diaper (that is, the front part P and/or the rear part Q). When the first joining part is provided in this manner, many wrinkles extending in the longitudinal direction y are formed in the exterior sheet 25, and the waist elastic member 33 or the body elastic member 34 can be made hardly to be seen from the outside of the exterior sheet 25. Specifically, in the exterior sheet 25, two kinds of joining parts, the first joining part and the second joining part, are formed, and therefore, a large number of fine wrinkles can be formed in the exterior sheet 25, thereby increasing the visual shielding effect of the exterior sheet 25.

It is also preferable that a plurality of the first joining parts are aligned in the width direction x and the longitudinal direction y in the body circumference part of the diaper, and a distance between the first joining parts in the width direction x is wider than that in the longitudinal direction y. Also by providing the first joining part in this manner, many wrinkles extending in the longitudinal direction y are formed in the exterior sheet 25 when the waist elastic member 33 or the body elastic member 34 contracts in the width direction x, and as a result, the waist elastic member 33 or the waist elastic member 34 can be made hardly to be seen from the outside of the exterior sheet 25.

Materials of members constituting the absorbent article of the present invention are explained. The top sheet is a sheet which is located on a wearer's side in wearing the absorbent article and preferably liquid-permeable. Examples of the top sheet include, for example, a nonwoven fabric formed from hydrophilic fibers such as cellulose, rayon and cotton; and a nonwoven fabric which is formed from hydrophobic fibers such as polyolefin (e.g., polypropylene, polyethylene), polyester (e.g., PET) and polyamide (e.g., nylon), and in which the hydrophobic fibers are hydrophilized with a surfactant on the surface thereof. As the top sheet, a woven fabric, a knitted fabric, a plastic film having pores may be also used.

The back sheet is a sheet which is located on an opposite side of the wearer, that is an exterior side, in wearing the absorbent article and preferably liquid-impermeable. Examples of the back sheet include, for example, a nonwoven fabric formed from hydrophobic fibers such as polyolefin (e.g., polypropylene, polyethylene), polyester (e.g., PET) and polyamide (e.g., nylon), and a plastic film. As the back sheet, a laminate of a nonwoven fabric and a plastic film may be also used. In the present invention, the meaning of "liquid-impermeable" includes water-repellent.

The pants member (the inner sheet and the exterior sheet) may be liquid-permeable or liquid-impermeable, and a sheet material usable for the top sheet or the back sheet can be used.

In the case of using a nonwoven fabric for the above sheet material, a spunbonded nonwoven fabric, an air-through nonwoven fabric, a point-bonded nonwoven fabric, a melt-blown nonwoven fabric, an air-laid nonwoven fabric, an SMS nonwoven fabric or the like is preferably used as the nonwoven fabric. In the exterior sheet (the nonwoven fabric laminate), since the respective the nonwoven fabric layers are joined to each other by heat-embossing, they preferably contain thermal fusion fibers such as polyolefin (e.g., polypropylene, polyethylene), polyester (e.g., PET) and polyamide (e.g., nylon).

The absorbent core is not particularly restricted as long as it absorbs excrement such as urine and the like. As the absorbent core, a clump of an absorbent material, which is formed into a predefined shape, may be used. The absorbent core may be wrapped with a sheet member such as paper (e.g., a tissue paper and a thin paper) and a liquid-permeable nonwoven fabric. Examples of the absorbent material contained in the absorbent core include, for example, a hydrophilic fiber such as a cellulose fiber (e.g., a crushed pulp fiber) and an absorbent polymer such as polyacrylic absorbent polymer, polyasparaginic absorbent polymer, cellulosic absorbent polymer, and stark-acrylonitrile absorbent polymer. The absorbent material may contain a thermal fusion fiber. The thermal fusion fiber may be hydrophilized with a surfactant or the like to increase affinity with a bodily fluid such as urine.

The absorbent material preferably contains a hydrophilic fiber in view of increasing absorption speed of urine or the like. In addition, in view of enhancing absorption capacity, the absorbent material preferably contains an absorbent polymer. Therefore, the absorbent core preferably contains both a hydrophilic fiber (especially a pulp fiber) and an absorbent polymer. In this case, the absorbent material is preferably obtained by mixing an absorbent polymer with a hydrophilic fiber assembly, or dispersing an absorbent polymer on a hydrophilic fiber assembly, for example.

The absorbent core may be a sheet-shaped absorbent body. Examples of the sheet-shaped absorbent body include an object which is formed to contain an absorbent polymer but not contain a pulp fiber between nonwoven fabrics. The sheet-shaped absorbent body formed in this manner enables high absorption capacity since it contains an absorbent polymer between nonwoven fabrics. In addition, since the sheet-shaped absorbent body does not contain a pulp fiber between nonwoven fabrics, it can be formed thin without being bulky.

As the sheet-shaped absorbent body, an absorbent fiber may be used for the absorbent material. Also in this case, the sheet-shaped absorbent body is formed thin without being bulky. Examples of the absorbent fiber include a fiber having a protonated carboxyl group or a carboxylate group. The absorbent fiber can be obtained by, for example, hydrolyzing an acrylic fiber, thereby converting a nitrile group contained in the acrylic fiber to a carboxylic group, as disclosed in Japanese Examined Patent Application Publication No. S52-42916. The carboxyl group contained in the absorbent fiber is preferably forms an alkaline metal salt or an ammonium salt. The absorbent fiber also can be prepared by immersing a hydrophilic fiber in acrylic acid to deposit acrylic acid on the surface of the fiber.

This application claims priority to Japanese Patent Application No. 2013-203773, filed on Sep. 30, 2013, the entire contents of which are incorporated by reference herein.

REFERENCE SIGNS LIST

1: a nonwoven fabric laminate
2, 49: a first nonwoven fabric layer
3, 45: a second nonwoven fabric layer
4, 43: a third nonwoven fabric layer
5: a fourth nonwoven fabric layer
6: a first joining part
7: a second joining part
11, 21: an absorbent article
12, 28: a top sheet
13, 29: a back sheet
14, 30: an absorbent core
24: a pants member
25: an exterior sheet
26: an inner sheet
33: a waist elastic member
34: a body elastic member
46, 50: a heat-embossing roll
47, 51: a flat roll
52: a nonwoven fabric laminate (a continuous body)

The invention claimed is:

1. An absorbent article comprising an exterior sheet formed of a plurality of nonwoven fabric layers, wherein
   the exterior sheet is located on an outer side of the absorbent article and has a first nonwoven fabric layer, a second nonwoven fabric layer and a third nonwoven fabric layer from the outer side of the absorbent article,
   the first nonwoven fabric layer, the second nonwoven fabric layer and the third nonwoven fabric layer are joined to each other at a first joining part by heat-embossing,
   the second nonwoven fabric layer and the third nonwoven fabric layer are further joined to each other at a second joining part by heat-embossing, and
   the first joining part and the second joining part have a different shape from each other.

2. The absorbent article according to claim 1, wherein an area of the one first joining part is larger than that of the one second joining part.

3. The absorbent article according to claim 1, wherein each of the first nonwoven fabric layer, the second nonwoven fabric layer and the third nonwoven fabric layer is made of a spunbonded nonwoven fabric or an air-through nonwoven fabric.

4. The absorbent article according to claim 3, wherein the first joining part has a shape that is shorter in an orientation direction of fibers constituting the nonwoven fabric than in an orthogonal direction thereof.

5. The absorbent article according to claim 1, wherein
   an elastic member is disposed to a skin-facing side of the exterior sheet, and
   the first joining part has a shape that is shorter in an extending direction of the elastic member than in an orthogonal direction thereof.

6. The absorbent article according to claim 1, wherein
   an elastic member is disposed to a skin-facing side of the exterior sheet, and
   a plurality of the first joining parts are aligned in an extending direction of the elastic member and an orthogonal direction thereof, and a distance between the first joining parts in the extending direction is wider than that in the orthogonal direction.

7. The absorbent article according to claim 1, wherein the absorbent article is a pants-type disposable diaper,
   an elastic member extending in a width direction of the diaper is disposed at a body circumference part of the diaper between the exterior sheet and an inner sheet provided on a skin-facing side of the exterior sheet, and the first joining part has a shape that is longer in a longitudinal direction of the diaper than in the width direction of the diaper.

8. The absorbent article according to claim 1, wherein the absorbent article is a pants-type disposable diaper, an elastic member extending in a width direction of the diaper is disposed at a body circumference part of the diaper between the exterior sheet and an inner sheet provided on a skin-facing side of the exterior sheet, and a plurality of the first joining parts are aligned in a longitudinal direction of the diaper and the width direction of the diaper, and a distance between the first joining parts in the width direction of the diaper is wider than that in the longitudinal direction of the diaper.

9. A nonwoven fabric laminate in which a first nonwoven fabric layer, a second nonwoven fabric layer and a third nonwoven fabric layer are laminated in this order, wherein the first nonwoven fabric layer, the second nonwoven fabric layer and the third nonwoven fabric layer are joined to each other at a first joining part by heat-embossing, the second nonwoven fabric layer and the third nonwoven fabric layer are further joined to each other at a second joining part by heat-embossing, and the first joining part and the second joining part have a different shape from each other.

10. The nonwoven fabric laminate according to claim 9, wherein an area of the one first joining part is larger than that of the one second joining part.

11. The nonwoven fabric laminate according to claim 9, wherein each of the first nonwoven fabric layer, the second nonwoven fabric layer and the third nonwoven fabric layer is made of a spunbonded nonwoven fabric or an air-through nonwoven fabric.

12. The nonwoven fabric laminate according to claim 11, wherein the first joining part has a shape that is shorter in an orientation direction of fibers constituting the nonwoven fabric than in an orthogonal direction thereof.

13. A process for producing a nonwoven fabric laminate, comprising the steps in the sequence set forth:

forming a third nonwoven fabric layer;

forming a second nonwoven fabric layer on the third nonwoven fabric layer;

heat-embossing the second nonwoven fabric layer and the third nonwoven fabric layer to join to each other at a second joining part;

forming a first nonwoven fabric layer on the second nonwoven fabric layer; and heat-embossing the first nonwoven fabric layer, the second nonwoven fabric layer and the third nonwoven fabric layer to join to each other at a first joining part, wherein the first joining part and the second joining part have a different shape from each other.

* * * * *